United States Patent
Dittrich

(10) Patent No.: US 12,367,964 B2
(45) Date of Patent: Jul. 22, 2025

(54) TRANSMISSION OF MEDICAL VIDEO DATA

(71) Applicant: Siemens Healthineers AG, Forchheim (DE)

(72) Inventor: Steffen Dittrich, Erlangen (DE)

(73) Assignee: Siemens Healthineers AG, Forchheim (DE)

( * ) Notice: Subject to any disclaimer, the term of this patent is extended or adjusted under 35 U.S.C. 154(b) by 19 days.

(21) Appl. No.: 18/359,203

(22) Filed: Jul. 26, 2023

(65) Prior Publication Data

US 2024/0038365 A1    Feb. 1, 2024

(30) Foreign Application Priority Data

Jul. 28, 2022  (DE) .................... 10 2022 207 747.4

(51) Int. Cl.
| | |
|---|---|
| *G16H 30/20* | (2018.01) |
| *G16H 10/60* | (2018.01) |
| *H04L 9/40* | (2022.01) |
| *H04N 7/18* | (2006.01) |

(52) U.S. Cl.
CPC ............ *G16H 30/20* (2018.01); *G16H 10/60* (2018.01); *H04N 7/183* (2013.01); *H04L 63/0428* (2013.01)

(58) Field of Classification Search
CPC ........ G16H 30/20; G16H 10/60; H04N 7/183; H04N 7/18; H04N 5/268; H04N 5/76; H04L 63/0428
See application file for complete search history.

(56) References Cited

U.S. PATENT DOCUMENTS

| | | | |
|---|---|---|---|
| 11,450,419 B1* | 9/2022 | Esman | G16H 20/13 |
| 11,678,011 B1* | 6/2023 | Fu | H04N 21/8549 |
| | | | 348/143 |
| 2002/0023172 A1* | 2/2002 | Gendron | H04L 67/568 |
| | | | 709/238 |
| 2002/0052866 A1* | 5/2002 | Wortmann | H04L 67/12 |
| 2002/0184527 A1* | 12/2002 | Chun | H04L 67/56 |
| | | | 726/4 |
| 2012/0317598 A1* | 12/2012 | Gilson | H04N 5/445 |
| | | | 725/32 |
| 2014/0096170 A1* | 4/2014 | Emerson | H04N 21/4223 |
| | | | 725/98 |
| 2014/0289611 A1 | 9/2014 | Norwood et al. | |

(Continued)

*Primary Examiner* — Fernando Alcon
(74) *Attorney, Agent, or Firm* — HARNESS, DICKEY & PIERCE, P.L.C.

(57) ABSTRACT

One or more example embodiments of the present invention relates to a method for transmitting medical video data via a network. According to one more example embodiments, medical video data is provided via at least one of a medical imaging modality or a hospital data system. The medical video data is held in a buffer. Furthermore, a network connection is established in the network from a terminal to the buffer via a web protocol. The medical video data is transmitted from the buffer to the terminal in at least one network data stream via the network connection via the web protocol. The medical video data is displayed on a display apparatus of the terminal. One or more example embodiments of the present invention further relates to a system for transmitting medical video data and a buffer and also a terminal for such a system.

20 Claims, 2 Drawing Sheets

(56) References Cited

U.S. PATENT DOCUMENTS

| | | | | |
|---|---|---|---|---|
| 2015/0178457 A1* | 6/2015 | Grimley | .............. | G06F 3/04817 |
| | | | | 705/3 |
| 2015/0304707 A1* | 10/2015 | Vadura | ............... | H04N 21/4135 |
| | | | | 725/25 |
| 2018/0110398 A1* | 4/2018 | Schwartz | ............. | A61B 1/0002 |
| 2018/0157915 A1* | 6/2018 | Sherry | ................... | H04N 21/84 |
| 2020/0162796 A1* | 5/2020 | Azuolas | ........... | H04N 21/23106 |
| 2020/0250826 A1* | 8/2020 | Cohen Maimon | ..... | G16H 30/20 |
| 2021/0158928 A1* | 5/2021 | Pereira | ................ | G06F 21/6245 |
| 2021/0336939 A1* | 10/2021 | Wiener | ...................... | G06F 8/65 |
| 2022/0053041 A1* | 2/2022 | Drako | ...................... | H04N 7/18 |
| 2022/0181020 A1* | 6/2022 | Keshavjee | ............. | G06V 10/28 |
| 2022/0208319 A1* | 6/2022 | Ansari | ................ | H04L 65/1073 |
| 2022/0353468 A1* | 11/2022 | Walia | ...................... | H04N 7/147 |
| 2022/0394327 A1* | 12/2022 | Sampson | ................ | H04L 67/06 |
| 2023/0100302 A1* | 3/2023 | Asai | ................... | A61B 1/00006 |
| | | | | 705/2 |
| 2023/0216947 A1* | 7/2023 | Bernardi | ................ | H04L 67/10 |
| | | | | 713/150 |
| 2024/0212812 A1* | 6/2024 | Vidyashankar Keresanthe | ........... | |
| | | | | G16H 30/40 |

\* cited by examiner

TRANSMISSION OF MEDICAL VIDEO DATA

CROSS-REFERENCE TO RELATED APPLICATION(S)

The present application claims priority under 35 U.S.C. § 119 to German Patent Application No. 10 2022 207 747.4, filed Jul. 28, 2022, the entire contents of which are incorporated herein by reference.

FIELD

One or more example embodiments relates to a method for transmitting medical video data in a network, such a system and also a terminal and a buffer for such a system.

RELATED ART

In video technology, usually at least the following steps are performed in order to transmit video signals. Initially, the video signals are read from a source, for example a camera or another recording device. Subsequently, the video signals are output in a further step into a sink, for example a monitor, a display or a data storage device. In practice, however, it is often not only desirable to have point-to-point connections in which a source is connected in each case to a sink but rather in many application cases it is also required that video signals are distributed from one or multiple sources to multiple sinks. Between the reading and the output of the video signals these video signals are in practice often also further processed, in other words for example enlarged, decreased in size, cut, converted into other frame rates, merged or the like.

In order to distribute video signals a suitable network is often used. For this purpose, previously video data, which is provided in the form of electrical signals for example at the output of a camera, is often converted via a hardware solution, in other words an adaptor, into a form that is suitable for the network. One example of this is HDBaseT.

Furthermore, it is known from practice to convert video data, which has been generated for example via software, using an additional operating software or configuration software into a standardised or proprietary transmission protocol and then to transmit this via the network. One example of this is SDVoE.

SUMMARY

Hitherto known solutions consequently always require an additional (hardware or software) component and consequently cannot be readily performed using the means that are usually installed on a terminal.

Consequently, an object of the present invention is to simplify the transmission of medical video data in a network.

This object is achieved by a method for transmitting medical video data in a network in accordance with claim 1, such a system for transmitting medical video data in a network and also a terminal and a buffer for such a system in accordance with the independent claims.

BRIEF DESCRIPTION OF THE DRAWINGS

One or more example embodiments are explained below with reference to the attached figures with the aid of exemplary embodiments. In this case, identical components are provided with identical reference characters in the different figures.

In general, the figures are not to scale. In the drawings.

DETAILED DESCRIPTION

Figure 1:
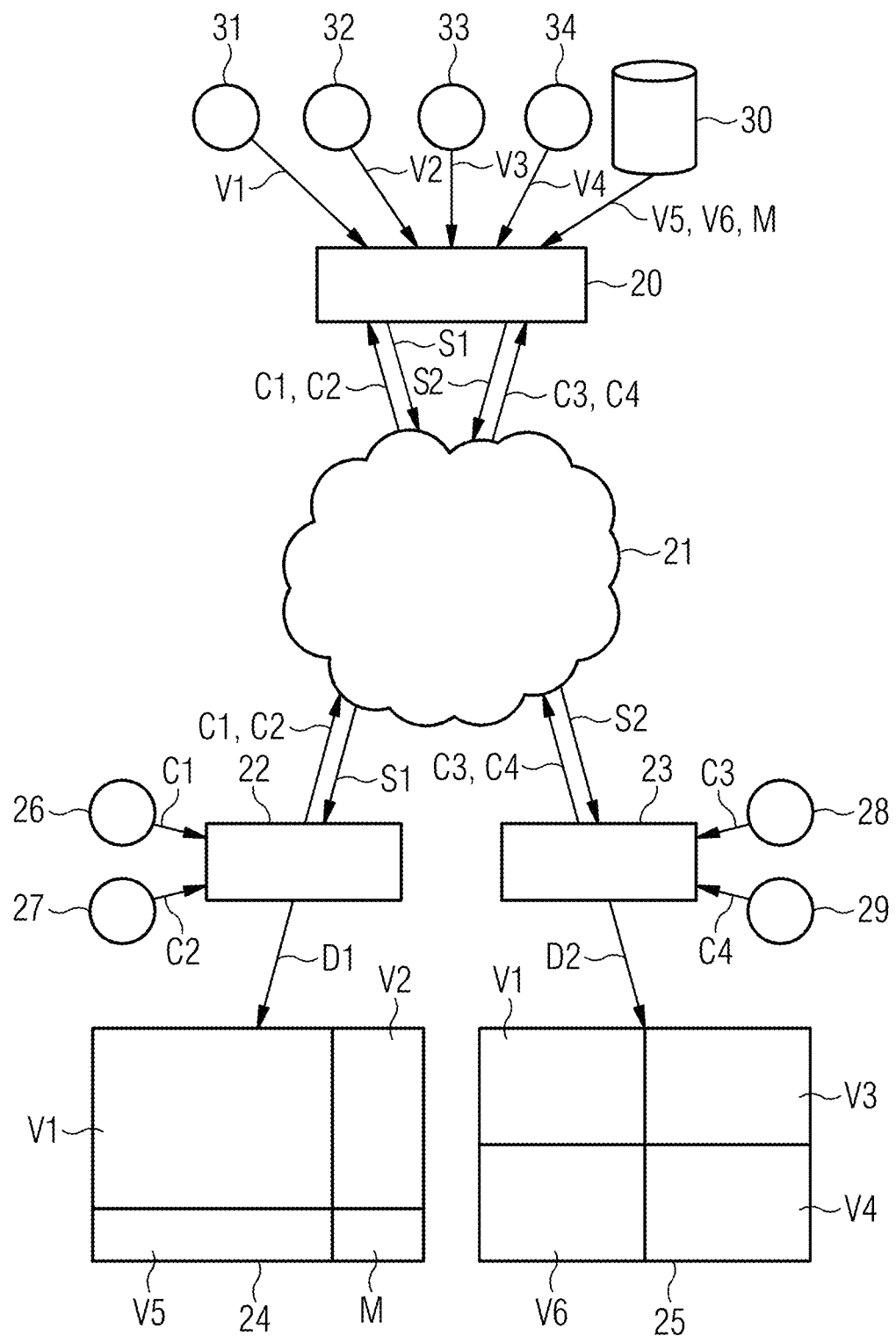
FIG. 1 shows a rough schematic block diagram for transmitting medical video data in accordance with one or more example embodiments.

One or more example embodiments relates to a method used so as to transmit medical video data via a network. For this purpose, in one step initially medical video data is provided via a medical imaging modality and/or a hospital data system. In a further step, the medical video data is held in a buffer. A network connection is established in the network from a, preferably remote, terminal to the buffer via at least one web protocol in a further step. Moreover, in one step, the medical video data is transmitted from the buffer to the terminal in at least one network data stream via the network connection via the web protocol. The medical video data is displayed in a further step on a display apparatus of the terminal.

The medical video data or video signals in this case comprise data that is acquired via medical imaging modality and consequently are provided quasi directly. Alternatively or in addition thereto, the medical video data was acquired beforehand via a medical imaging modality and stored and made available in the hospital data system. The hospital data system is connected for this purpose for example to the medical imaging modality and can comprise for this purpose in particular an in-house network. Moreover, the hospital data system has a suitable data storage device in which inter alia the medical video data is stored. The hospital data system can be implemented for example as PACS (picture archiving and communication system).

The medical imaging modality can be for example a CT device, an MRT device, an X-ray device, an ultrasonic device or the like. The medical video data or video signals accordingly comprise in particular measuring data of the modalities from which are generated images or image series preferably from the interior of a patient.

The medical video data is stored in the buffer prior to the transmission and where applicable is further modified and/or compiled for the transmission. This can be performed for example via a control unit or computer unit for controlling the buffer. This means that the buffer consequently acts as a server in combination with the controller.

Accordingly, a network connection to the buffer via the network can be requested by a terminal or the receiver of the medical video data. In this case, the connection can be established via a standard network protocol, such as for example the Ethernet protocol, TCP/IP and/or the like. Accordingly, the network can be for example an Ethernet-based network, the internet and/or the like. In this case, the network connection is preferably produced via multiple network nodes. The network connection can fundamentally however also be realised in a direct (point-to-point) manner.

The terminal can fundamentally be any arbitrary terminal that is suitable for receiving the medical video data via the network via the web protocol and for displaying via a display apparatus. The terminal can be for example a tablet, a smartphone, a suitable monitor, a PC having a connected monitor, which is not suitable in itself, or the like. In addition, it is also possible using an adaptor, such as for example a stick having a microprocessor or an integrated circuit, to augment an arbitrary monitor, which is not suitable in itself for receiving, in that the stick performs the conversion of the network data stream to the medical video data.

Moreover, fundamentally any arbitrary web protocol that is suitable for the transmission of video data is used as the web protocol. For example, it is possible to use RTP. However, in order to establish the connection it is preferred that HTTP or particularly preferably HTTPS is used. Furthermore, the specific video request, for example in relation to content, resolution, frame rate etc. is sent in particular to the buffer, which is acting as a server, so that this can be offered correctly. In other words, in particular multiple standardised web protocols are used in order to realise the transmission.

The transmission of the medical video data and optionally further data is performed via the network in a network data stream, in other words in particular in a stream of data packets, preferably in a manner defined by the web protocol.

The system mentioned in the introduction for transmitting medical video data in a network comprises in particular the components that are required for the implementation of the above-described method. In other words, the system comprises a medical imaging modality and/or a hospital data system for providing medical video data. Moreover, the system comprises a buffer for holding the medical video data.

A network that is likewise included is configured so as to establish a network connection from a, preferably remote, terminal to the buffer via a web protocol. In this case, the medical video data is transmitted from the buffer to the terminal in at least one network data stream via the network connection of the network via the web protocol and is displayed on a display apparatus of the terminal.

The terminal mentioned in the introduction is designed so as to transmit medical video data in a system in accordance with one or more example embodiments of the present invention. The terminal in other words has in particular corresponding connection interfaces to the network and is configured so as to establish a network connection to the buffer. Moreover, the terminal is configured so as to generate video data streams from the network data streams and the video data streams can be reproduced on the display apparatus of the terminal.

The buffer mentioned in the introduction is designed so as to transmit medical video data in a system in accordance with one or more example embodiments of the present invention. The buffer therefore in particular includes a data storage device and also corresponding connection interfaces to the network and is configured so as to convert the medical video data streams into network data streams and so as to transmit them via the network connection to a terminal.

A large proportion of the above-mentioned components of the system can be realised entirely or in part in the form of software modules in a processor of a corresponding computer system, for example of a terminal or a control facility of a buffer. A largely software-based realisation has the advantage that computer systems that are already previously used can be retrofitted in a simple manner by a software update in order to function in the manner in accordance with one or more example embodiments of the present invention. In this respect, the object is also achieved by a corresponding computer program product having a computer program, which can be loaded directly into a computer system, having program sections in order to perform the steps of the method in accordance with one or more example embodiments of the present invention if the program is executed in the computer system. Such a computer program product in addition to the computer program can where necessary comprise additional components such as for example a documentation and/or additional components, and also hardware components such as for example hardware keys (dongles etc.) in order to use the software.

For the transport to the computer system or to the control facility and/or to the storage device at or in the computer system or the control facility, it is possible to use a computer-readable medium, for example a memory stick, a hard drive or another transportable or fixedly installed data carrier on which are stored the program sections of the computer program, which can be read and performed by a computer system. The computer system can have for example for this purpose one or multiple cooperating microprocessors or the like.

Further, particularly advantageous embodiments and developments of the invention are provided in the dependent claims and also the subsequent description, wherein the claims of one claim category can also be developed in a similar manner to the claims and description parts with regard to another claim category and in particular also individual features of different exemplary embodiments or variants can be combined to new exemplary embodiments or variants.

One or multiple of the standardised protocols Ethernet protocol, TCP/IP, HTTP or HTTPS is preferably used as the web protocol. This has the advantage that it is not necessary to install additional software on the terminal neither for the production of the connection nor for the display of the medical video data. Conversely, drivers, firmware, web browsers etc. can be used that are usually already installed on a terminal.

The terminal is preferably arranged remote from the buffer, the medical imaging modality and/or from the hospital data system. In this case, in which cables such as for example HDMI no longer suffice for the transmission paths, the transmission is realised by one or more example embodiments of the present invention in a simpler and more cost-effective manner with respect to the prior art.

The medical video data from multiple different video data streams is preferably transmitted. This means that the medical video data comprises for example video signals of different views from different viewing angles having different contrast and/or having different functional features that have been acquired by an imaging modality. Alternatively or in addition thereto, the medical video data can also comprise data of different imaging modalities.

The network data streams are preferably compiled according to a user specification from the different video data streams and particularly preferably adapted dynamically to the user specification. This means that the user can for example select which medical video data and which additional data is to be transmitted according to each application case. Moreover, the user can for example specify quality or resolution and/or frame rate (refresh rate) of the medical video data that is to be transmitted. It is consequently preferably possible depending on the size that is requested by the user on the display apparatus to also adapt the resolution of the video signals that are to be transmitted.

According to these stipulations, the buffer or the controller of the buffer can compile the data for the respective terminal or the receiver. For this purpose, a website is preferably generated that as content has the data that is to be transmitted. The website and its contents, in other words in particular the medical video data, are in this case particularly preferably generated dynamically in the buffer according to the user specifications.

Control data, which particularly preferably comprises the user specifications, is preferably transmitted via the web protocol from the terminal for this purpose to the buffer. This is therefore a return channel that transmits control signals or control commands such as for example keyboard inputs, mouse inputs, touch pad inputs via the network connection to the buffer. This renders possible in a simple manner a dynamic control when the data, which is to be transmitted, is being compiled.

The medical video data is preferably transmitted from the buffer to multiple terminals that are particularly preferably remote from one another. This means that the buffer holds an accordingly large quantity of medical video data and if necessary additional data or retrieves the video data in a timely manner from the medical imaging modality or from the hospital data system in order to be able to transmit the corresponding data to the respective terminals.

In this case, it is preferred that differently compiled network data streams, which can also comprise in particular different medical video data, are transmitted to different terminals preferably for each respective, in other words individual, user specification. As a consequence, the medical video data that is of particular relevance to the user is displayed to each user. This can be completely different views, different time periods of a video or the like depending on the individual requirements even for medical video data from the same patient.

It is preferred that additional further data is transmitted that particularly preferably comprises data with regard to the acquisition, in other words meta data or control parameters with regard to the acquisition, patient data and/or simple image data.

It is possible via the data with regard to the acquisition for the user to take into consideration firstly the exact settings of the imaging modality when making a finding. Secondly, they can adopt particularly effective control parameters for future acquisitions.

The patient data renders it possible for the user to set the medical video data for a finding in the right context. The patient data can comprise relevant values for the finding, such as for example age, weight, sex, blood values, pulse frequency, blood pressure or the like.

If only one static image (still image) is required by the user, it can preferably be transmitted as such, in other words not as part of an image series of the video data. As a consequence, advantageously the data quantity that is to be transmitted is reduced in comparison to the video signal.

Since medical video data is usually sensitive data of the patient, the transmission is preferably performed in an encrypted manner. In this case, the encryption can be performed using known encryption algorithms, such as for example via the SSL protocol (secure socket layer).

This is in particular relevant if the data leaves an essentially self-contained medical data unit, in other words for example a hospital in-house network via a potentially unsecured, where applicable public, network such as for example the internet.

Alternatively or preferably in addition to the simple encryption, the network connection is a secured data connection such as for example a virtual private network (VPN). It is possible via a VPN to realise a secure connection from the terminal to the self-contained medical data unit, in particular to the buffer, via unsecured transmission paths such as the internet.

For a terminal that is located outside the self-contained medical data unit it is particularly preferred to perform a two-factor authentication prior to the network connection to the buffer being produced.

Fundamentally, one or more example embodiments of the present invention therefore renders it possible to transmit the medical video data from the buffer to a suitable terminal via the usually installed browser without further software. For increased security requirements, it can be required in certain circumstances to install a VPN client on the terminal. However, this is also common and easily accessible software with the result that one or more example embodiments of the present invention clearly simplifies the transmission of medical video data.

FIG. 1 illustrates in an exemplary manner a system 100 in accordance with one or more example embodiments of the present invention for transmitting medical video data V1, V2, V3, V4, V5, V6 via a network 21 in a schematic block diagram. The medical video data V1, V2, V3, V4 is acquired here by four different medical imaging modalities 31, 32, 33, 34 and is transmitted into the buffer. The medical imaging modalities 31, 32, 33, 34 can be for example a CT device, an MRT device, an X-ray device, an ultrasound device or the like.

In this case, a first modality 31 generates a first set of medical video data V1, a second modality 32 generates a second set of medical video data V2 etc. Fundamentally, it is however also possible for an individual medical imaging modality to already generate multiple sets of medical video data, for example different views, in the course of an acquisition.

Furthermore, a fifth and a sixth set of medical video data V5, V6 are stored in a hospital data system 30, the data is retrieved from there and transmitted into the buffer 20. The hospital data system 30 comprises for this purpose a data storage device for the longer-term storage of the additional data M and the video data V5, V6 that are acquired in the hospital. The data storage device in this case is dimensioned corresponding to the data quantities that arise in the hospital.

Moreover, the hospital data system 30 comprises data connections to the imaging modalities 31, 32, 33, 34 and also where applicable data connections to individual display apparatuses in the hospital and also a data connection to the buffer 20.

Moreover, additional data M is stored in the hospital data system 30 and after retrieval the data is likewise transmitted into the buffer 20. The additional data M comprises data with regard to the acquisition, in other words meta data or control parameters with regard to the acquisition, patient data and/or simple image data.

The medical video data V1, V2, V3, V4, V5, V6 and the additional data M for the medium term are stored in the buffer 20 for the transmission. The buffer 20 is dimensioned for this purpose depending upon the requirements, in other words depending on the required transmission capacity. The buffer can be designed for example as a server having a storage unit and a processor unit that controls the transmission and compilation of the data.

If medical video data V1, V2, V3, V4, V5, V6 is requested by a terminal 22, 23, the buffer 20 transmits the video data V1, V2, V3, V4, V5, V6 and if necessary the additional data M via the network 21 and converts the data for this purpose into at least one network data stream S1, S2. This usually means that the medical video data V1, V2, V3, V4, V5, V6 is distributed to individual data packets and for example is sent via an Ethernet protocol and/or TCP/IP via the network 21. The network 21 can be fundamentally the hospital network in order to display the medical video data V1, V2, V3, V4, V5, V6 for example in a hospital diagnostic room that is remote from the medical imaging modalities 31, 32, 33, 34.

It is preferred that the network data streams S1, S2 are however transmitted via the internet, in other words a public and unsecured network, via Ethernet protocol and/or TCP/IP in order to display the data streams on external terminals 22, 23 outside of the hospital, in other words outside of a self-contained medical data unit.

The transmission is performed in the network 21, preferably via multiple network node points, via known routing or addressing protocols.

The terminals 22, 23 are connected for this purpose to the network 21 and via the network receive the network data streams S1, S2 and display the network data streams on a display apparatus 24, 25 that is allocated in each case to a terminal. The terminals 22, 23 can be for example a tablet, a smartphone, a suitable monitor, a PC having a connected monitor that is not suitable in itself or the like. In addition, it is also possible using an adaptor, such as for example a stick having a microprocessor or an integrated circuit, to augment an arbitrary monitor, which is not suitable in itself for receiving. In order to display the data V1, V2, V3, V4, V5, V6, M the terminal 22, 23 preferably has a customary web browser.

The terminals 22, 23 in this exemplary embodiment additionally offer the possibility to acquire user specifications as control data C1, C2, C3, C4 via input devices 26, 27, 28, 29. The terminals 22, 23 for this purpose in each case have a keyboard 26, 28 and a mouse 27, 29.

In this case, the control data C1, C2 of a first terminal 22 includes different user specifications to the control data C3, C4 of a second terminal 23. All the control data C1, C2, C3, C4 transmits via the network 21 in a return channel to the buffer 20. The buffer 20 compiles different network data streams S1, S2 depending on the control data C1, C2, C3, C4 for the first terminal 22 or the second terminal 23. This is performed for example by virtue of the fact that a website is generated dynamically in the buffer 20 for the respective network data stream S1, S2 according to the user specifications. In this case, in particular also the resolution of the medical video data V1, V2, V3, V4, V5, V6 is adapted in dependence upon the desired display size of the respective data. As a consequence, advantageously the data volume that is to be transmitted is kept as low as possible at identical viewing quality.

The website that is generated in the buffer 20 is preferably displayed via a web browser or web client. It is demonstrated in an exemplary manner on the first display apparatus 24 of the first terminal 22 that a first set of medical video data V1 is displayed as comparatively large in the left-hand side upper corner, while a second set of medical video data V2 is mapped in the right-hand side upper area as a vertical bar and a fifth set of medical video data V5 is displayed on the left-hand side lower region as a horizontal bar. Moreover, in the corner on the lower right-hand side for example the acquisition parameter that is used for the acquisition of the first set of medical video data V1 is displayed as additional data M.

In contrast, on the second display apparatus 25 four sets of medical video data V1, V3, V6, V4 are displayed in the left-hand side upper, right-hand side upper, left-hand side lower or right-hand side lower area with identical size.

The user can therefore freely select the size and position in which they want to display the medical video data and, if necessary, the additional data. Moreover, they can specify which set or data stream of the medical video data V1, V2, V3, V4, V5, V6 they would like to display.

An establishment of the connection is usually initialised on the part of the terminal 22, 23. For this purpose, the terminal preferably produces a connection via a virtual private network (VPN) to the buffer 20. Moreover, the transmitted data is preferably encrypted both on the part of the respective terminal 22, 23 as well as on the part of the buffer 20 via a known protocol such as for example SSL in order to also ensure sufficient security in the event of potentially sensitive data.

Figure 2:
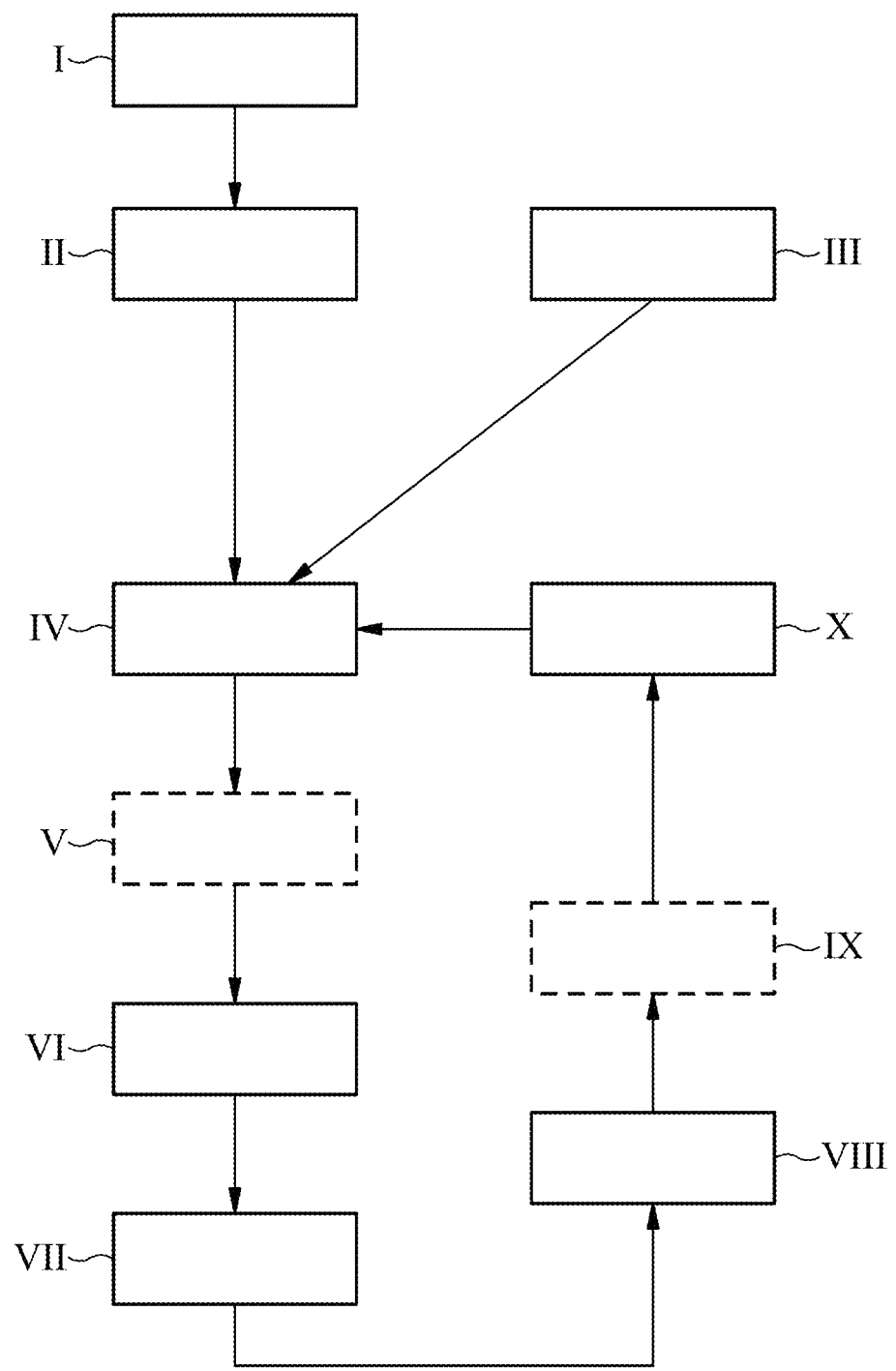
FIG. 2 shows a schematic flow chart for transmitting medical video data in accordance with one or more example embodiments.

FIG. 2 illustrates schematically a flow chart of an exemplary embodiment of a method in accordance with one or more example embodiments of the present invention for transmitting medical video data via a network.

In a first step I, medical video data V1, V2, V3, V4 is acquired from medical imaging modalities 31, 32, 33, 34.

In a second step II, the medical video data V1, V2, V3, V4 is transmitted into the buffer 20 and stored there.

In a third step III, medical video data V5, V6 and additional data M is transmitted from a hospital data system 30 into the buffer 20 and stored there.

In a further step IV, the medical video data V1, V2, V3, V4, V5, V6 and if necessary the additional data M is compiled for a transmission according to the user specifications or the control data C1, C2 and is converted into a first network data stream S1.

Optionally, in a further step V an encryption of the first network data stream S1 can be performed. In this case, the encryption can be realised for example via an SSL protocol and/or via a virtual private network (VPN).

In a further step V, the first network data stream S1 is transmitted via known web protocols such as the Ethernet protocol and/or TCP/IP to the first terminal 22.

After receiving at the first terminal 22, the first network data stream S1 is decrypted, converted back and displayed as medical video data V1, V2, V5 and also the additional data M is displayed on the first display apparatus 24 that is allocated to the first terminal 22, preferably via a web browser.

It is preferred that via the web browser in a further step VIII, user specifications that are made by keyboard 26 or by mouse 27 are acquired and converted into first control data C1, C2.

The first control data C1, C2 is encrypted in a further optional step IX as already described above.

In a yet further step X, the first control data C1, C2 is transmitted via the network 21 back to the buffer 20. In the buffer 20, the first control data C1, C2 is used in order to compile the user specifications that correspond to the first network data stream S1. The compilation first of the network data stream S1 is performed therefore dynamically in dependence upon the user specifications C1, C2.

Even if the above-described exemplary embodiments of a method in accordance with the invention for transmitting medical video data has only been performed for the first terminal 22 in detail it is clear that the method can also be used within the scope of the expertise of the person skilled in the art fundamentally for an arbitrary number of terminals.

Finally, reference is again made to the fact that the apparatuses and method that are described above in detail are only exemplary embodiments that can be modified in various ways by the person skilled in the art without departing from the scope of the invention. Furthermore, the use of the indefinite article "a" or "an" does not rule out that the relevant features can also be provided multiple times.

Likewise, the terms "device", "system", "apparatus", "unit" do not rule out that these are made of multiple components that—if not otherwise described—if necessary can also be spatially distributed.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "on," "connected," "engaged," "interfaced," and "coupled." Unless explicitly described as being "direct," when a relationship between first and second elements is described in the disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" on, connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

It is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed above. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments. The present invention may, however, be embodied in many alternate forms and should not be construed as limited to only the embodiments set forth herein.

In addition, or alternative, to that discussed above, units and/or devices according to one or more example embodiments may be implemented using hardware, software, and/or a combination thereof. For example, hardware devices (e.g., a terminal) may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a terminal including a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device (e.g., a terminal), may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one example embodiment relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

The invention claimed is:

1. A method for transmitting medical video data via a network, the method comprising:
   providing medical video data from multiple different video data streams via at least one of a medical imaging modality or a hospital data system;
   holding the medical video data in a buffer;
   establishing a network connection in the network from a terminal to the buffer via a web protocol;
   transmitting the medical video data from the multiple different video data streams, from the buffer to the terminal in at least one network data stream via the network connection via the web protocol, wherein the at least one network data stream is compiled from the multiple different video data streams based on a user specification and the at least one network data stream is adapted dynamically to the user specification; and
   displaying the medical video data on a display apparatus of the terminal,
   wherein the transmitting includes transmitting control data including the user specification via the web protocol from the terminal to the buffer, and
   the user specification includes at least one of an identification of the medical video data from the multiple different video data streams, a quality or resolution of the medical video data, a frame rate or refresh rate of the medical video data, or a resolution of the medical video data.

2. The method of claim 1, wherein the web protocol includes at least one of an Ethernet protocol, TCP/IP, HTTP or HTTPS.

3. The method of claim 1, wherein the transmitting transmits the medical video data to multiple terminals.

4. The method of claim 3, wherein network data streams that are compiled differently depending on the respective user specification are transmitted to different terminals.

5. The method of claim 1, wherein the transmitting transmits further data including data related to at least one of an acquisition, patient data or simple image data.

6. The method of claim 1, wherein the transmitting is performed in an encrypted manner.

7. A system for transmitting medical video data in a network, the system comprising:
   at least one of a medical imaging modality or a hospital data system configured to provide medical video data from multiple different video data streams;
   a buffer configured to hold the medical video data; and
   a network configured to establish a network connection from a terminal to the buffer via a web protocol, wherein
   the medical video data from the multiple different video data streams is transmitted from the buffer to the terminal in at least one network data stream via the network connection via the web protocol,
   the at least one network data stream is compiled from the multiple different video data streams based on a user specification and the at least one network data stream is adapted dynamically to the user specification, and
   the at least one network data stream is displayed on a display apparatus of the terminal,
   wherein the user specification includes at least one of an identification of the medical video data from the multiple different video data streams, a quality or resolution of the medical video data, a frame rate or refresh rate of the medical video data, or a resolution of the medical video data.

8. A terminal for the system for transmitting medical video data of claim 7.

9. A buffer for the system for transmitting medical video data of claim 7.

10. A non-transitory computer readable storage medium comprising instructions, when executed by a computer, cause the computer to perform the method of claim 1.

11. The system of claim 7, wherein the medical video data is transmitted to multiple terminals.

12. The system of claim 11, wherein network data streams that are compiled differently depending on the respective user specification are transmitted to different terminals.

13. The method of claim 2, wherein the transmitting transmits further data including data related to at least one of an acquisition, patient data or simple image data.

14. The method of claim 4, wherein the transmitting transmits further data including data related to at least one of an acquisition, patient data or simple image data.

15. The method of claim 14, wherein the transmitting transmits control data via the web protocol from the terminal to the buffer and the control data.

16. The method of claim 15, wherein the transmitting is performed in an encrypted manner.

17. The method of claim 1, further comprising:
   performing a two-factor authentication prior to establishing the network connection in the network from the terminal to the buffer via the web protocol.

18. The method of claim 1, further comprising:
   generating a website based on the user specification, the website including the at least one network data stream adapted to the user specification,
   wherein the website generated is displayed via a web browser.

19. The system of claim 7, wherein the terminal is configured to perform a two-factor authentication prior to establishing the network connection from the terminal to the buffer via the web protocol.

20. The system of claim 7, wherein the buffer is further configured to generate a website based on the user specification, the website including the at least one network data stream adapted to the user specification,
   the website generated is displayed via a web browser.

* * * * *